Figure 5A:
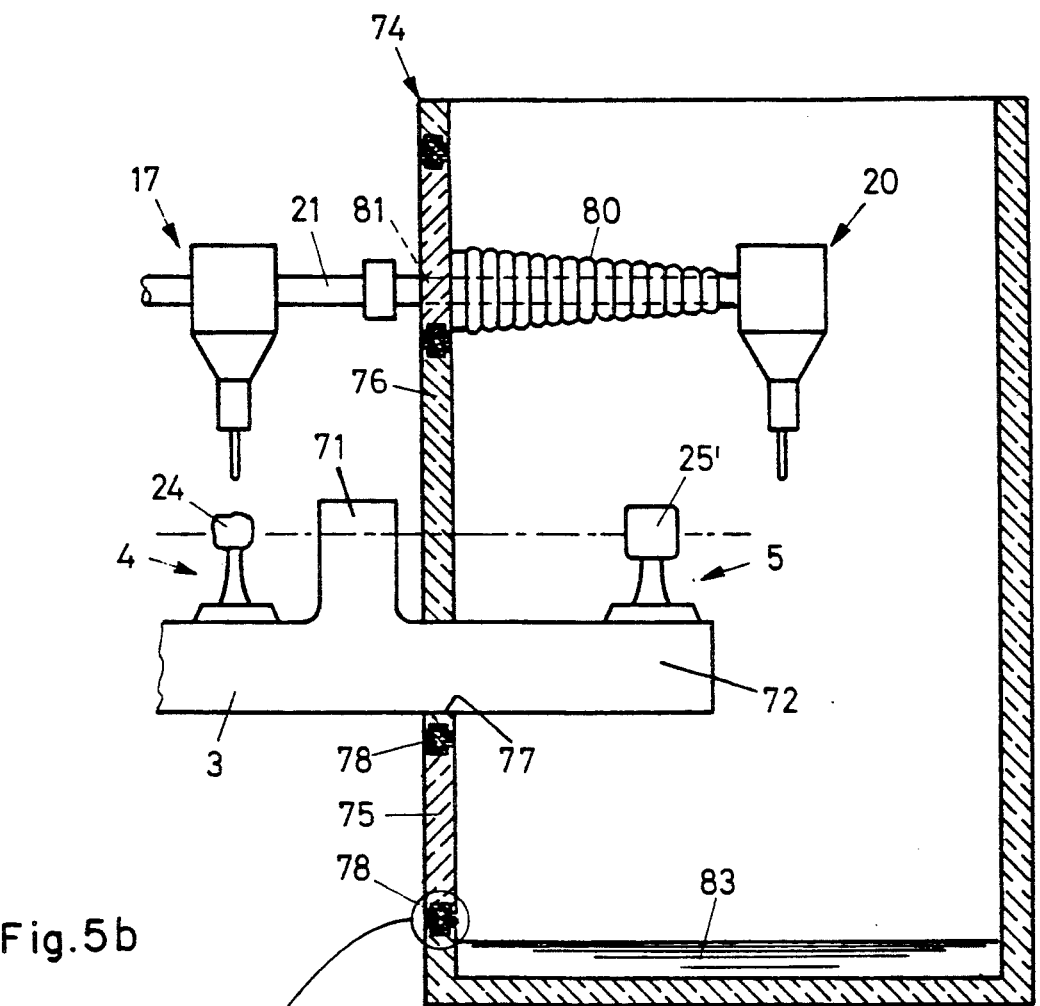

United States Patent [19]
Eidenbenz et al.

[11] Patent Number: 5,135,393
[45] Date of Patent: Aug. 4, 1992

[54] PROCESS AND APPARATUS FOR PRODUCING FABRICATED PARTS IN DENTISTRY

[75] Inventors: Stefan Eidenbenz, Zurich; Claude Nowak, Wettingen, both of Switzerland

[73] Assignee: Mikrona Technologie AG, Spreitenbach, Switzerland

[21] Appl. No.: 537,186

[22] Filed: Jun. 12, 1990

[30] Foreign Application Priority Data

Jun. 13, 1989 [CH] Switzerland ............ 02224/98

[51] Int. Cl.$^5$ ............................................. A61C 19/00
[52] U.S. Cl. ............................................. 433/53; 433/50; 409/121; 409/124
[58] Field of Search ............. 433/49, 50, 51, 52, 433/53, 75, 76; 409/85, 116, 121, 94, 87, 88, 89, 90, 124

[56] References Cited

U.S. PATENT DOCUMENTS

| | | | |
|---|---|---|---|
| 361,131 | 4/1887 | Carlinet | 409/90 |
| 4,403,961 | 9/1983 | Gurney | 433/213 |

*Primary Examiner*—Cary E. O'Connor
*Attorney, Agent, or Firm*—Egli International

[57] ABSTRACT

The apparatus has a copying mechanism (1), which is mounted in a support fork (2) and comprises a feeler (17) and a toolholder (20). The copying mechanism (1) is supported on a support fork (2), which is arranged swivellably and displaceably on a foundation body. With the copying mechanism (1) is associated a rocker (3), which carries a pattern station (4) and a fabricated part station (5). On the stations (4, 5) are synchronously and rotatably mounted a pattern (24) and a fabricated part (25). Due to the fact that with the pattern (24) and the fabricated part (25) are associated two movement axes, namely axis (26) and the rocker swivel axis (23), it is possible to sense patterns having a random three-dimensional shape and corresponding fabricated parts can be copied.

16 Claims, 3 Drawing Sheets

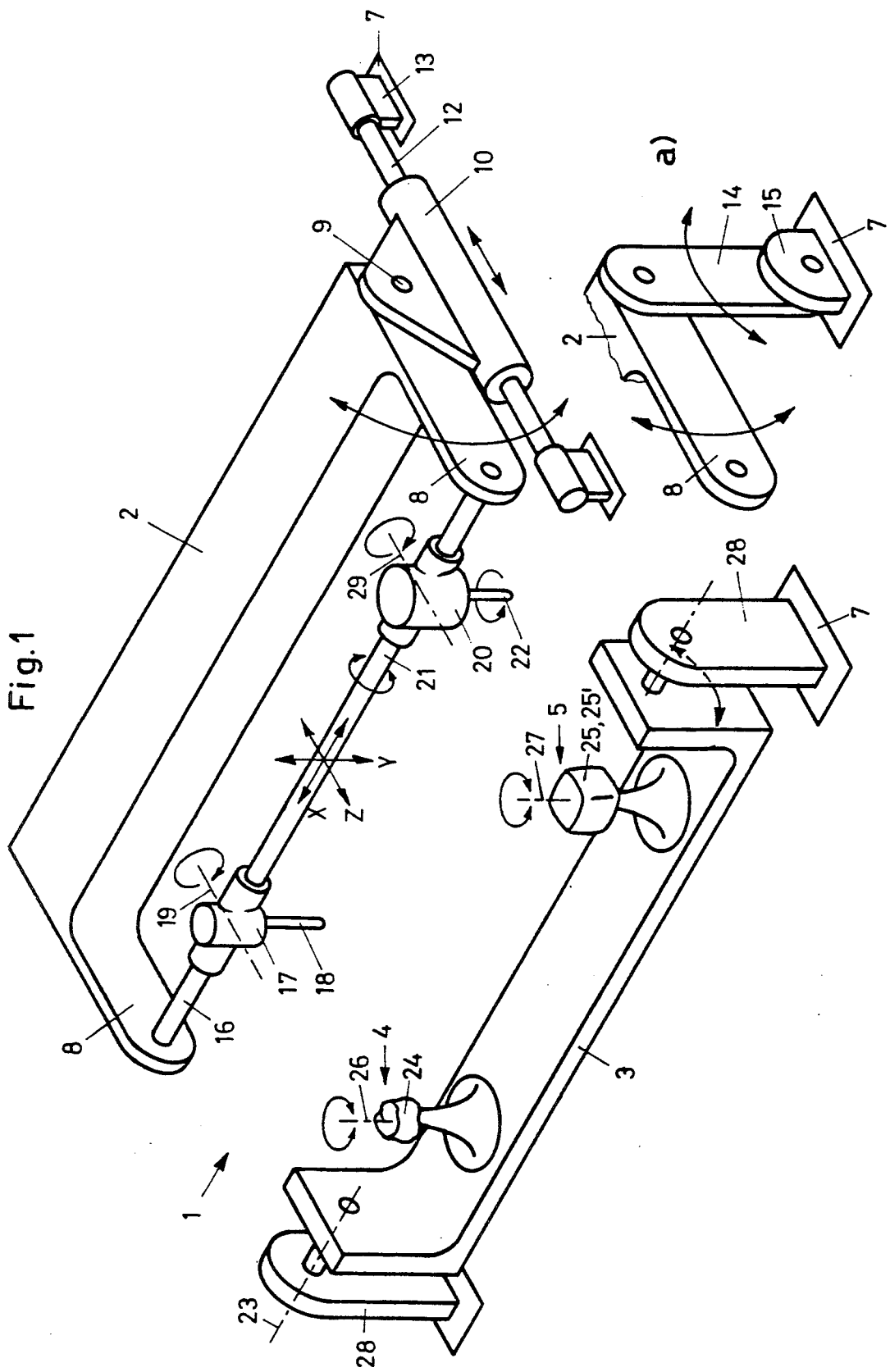

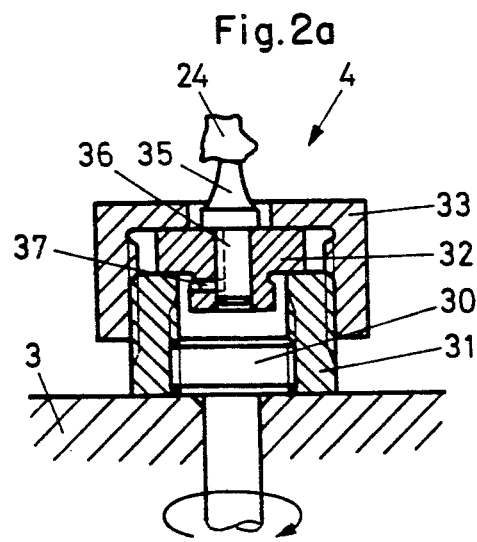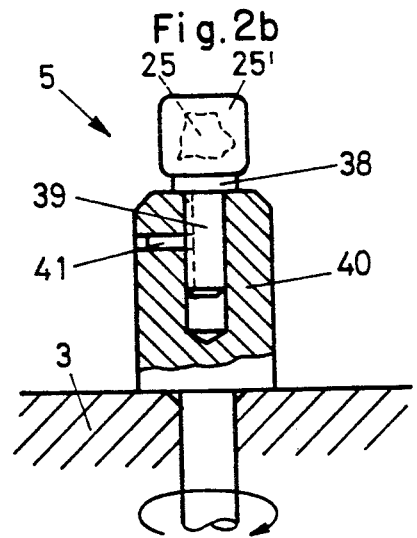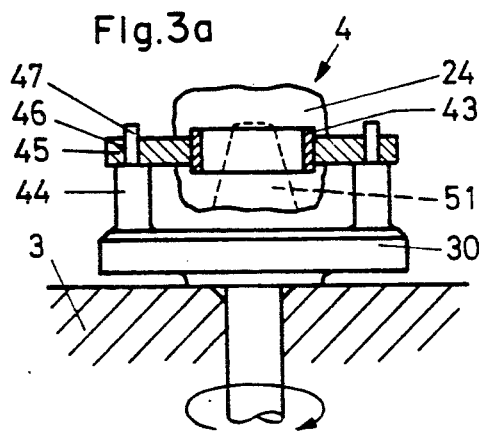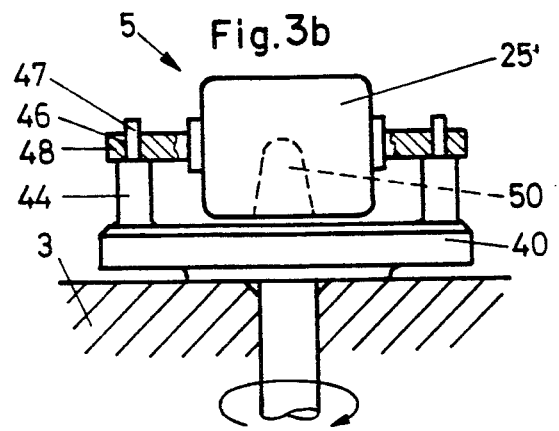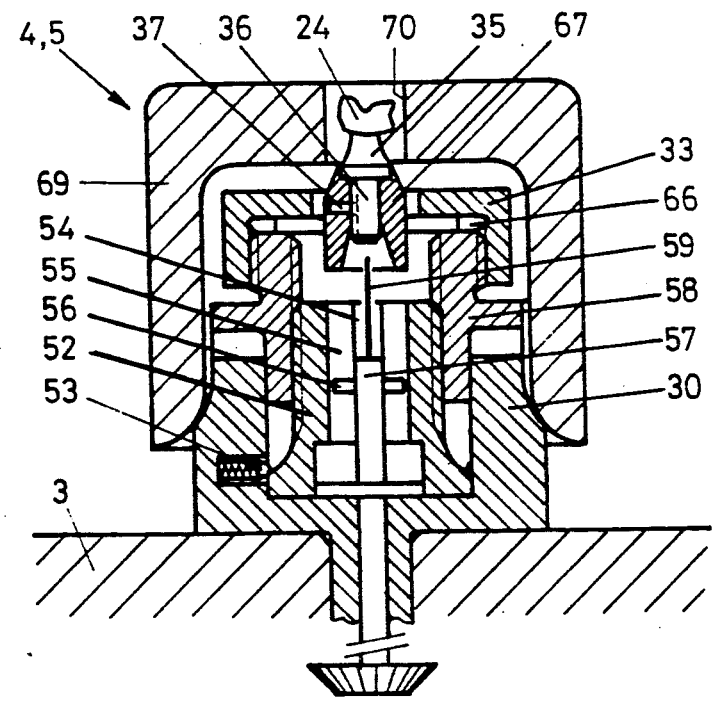

PROCESS AND APPARATUS FOR PRODUCING FABRICATED PARTS IN DENTISTRY

The invention relates to a process for producing a fabricated or shaped part machined using copying technology and in particular for producing inlays, onlays and crowns in dentistry, in which a pattern is sensed with a feeler pin and whose displacement or deflection is transferred to a motor driven machining tool for the machining of the fabricated part from a blank, as well as to an apparatus for performing this process.

The long known copying method is used for producing workpieces having a complicated three-dimensional shape. A pattern is mechanically sensed by means of a feeler pin. The displacements of the feeler pin are transmitted to a motor driven machining tool, which in a machining operation, e.g. milling or grinding, rough works from a blank a fabricated part identical to the pattern. In the case of large machine tools the transfer of the feeler pin displacements to the machining tool takes place by means of a control unit and it is also subsequently possible to produce larger or smaller copies of the pattern.

Such complicated control units are unnecessary for producing small fabricated parts. In this case the displacements of the feeler pin are directly transferred to the machining tool, the feeler pin and the toolholder being mechanically firmly coupled together.

The invention relates to a copying process and a copying apparatus of the second-mentioned type, i.e. with direct mechanical transfer of the feeler pin displacements to the machining tool, which makes it possible to produce small fabricated parts, such as are e.g. used in precision mechanics. However, such apparatuses have a very simple construction and normally have no more than three movement or motion axes. However, if fabricated parts with a complicated three-dimensional shape are to be produced, the relatively small number of movement axes is not sufficient for copying such a fabricated part. Such fabricated parts are e.g. required for inlays, onlays and crowns in dentistry.

As dental analgans are being increasingly frowned upon as filling materials as a result of the use of mercury, apart from the known gold fillings and crowns new materials have been introduced. The latter include oxide ceramic materials, which have a very considerable hardness and whose other characteristics also make them suitable for restoring the shape and function of a tooth.

It is relatively difficult to process such very hard materials. If the defect replacement, i.e. the inlay, onlay or crown is produced in a negative mould and then sintered, the sintering process leads to considerable divergences, e.g. due to shrinkage compared with the original shape and as a result said replacement must be reworked.

In order to speed up the production of such defect replacement it is known, following the preparation of the tooth, to optically measure the defect point and store the measured values in a computer. On the basis of this impression of the defect point a ceramic replacement can be worked as a result of the stored optical impression until it has acquired its final shape. However, as it is not possible to optically measure a random number of points, a dimensional inaccuracy remains, which can have a disadvantageous effect in the case of prolonged use of the filling.

The problem of the present invention, using a copying process of the second-mentioned type, is to produce defect replacements and other fabricated parts, which are characterized by a high accuracy and which in particular as replacements in dentistry can be so accurately machined that when inserted in the tooth it is possible to achieve a gap between the dental material and the replacement which is below the critical gap width for the formation of caries.

According to the invention this problem is solved in that two movement axes are associated with the pattern and the fabricated part for determining the complete surface of the pattern and the fabricated part produced from it and as a result the pattern and the fabricated part can be moved about their axes and about a swivel axis intersecting said axes and at right angles thereto. Preferably the pattern and the fabricated part are rotated synchronously about their axes. Appropriately the pattern and the fabricated part are moved manually about their movement axes. Due to the fact that additional movement axes are associated with the pattern and the fabricated part, it is also possible to perfectly sense fabricated parts having very complicated shapes, so that the prerequisite for the accurate production of the fabricated part is satisfied.

The invention also relates to an apparatus solving the problem of performing the process of the invention in an optimum manner. This is achieved in that the pattern and the fabricated part or fabricated part blank are rotatably mounted in a rocker and are interconnected in a mechanical and synchronously movable manner, said rocker being supported on the foundation body and can be swivelled about a swivel axis, which is at right angles to the rotation axes of the pattern and the fabricated part and intersects the same.

The invention is described in greater detail hereinafter relative to a non-limitative embodiment and the attached drawings, wherein show:

FIG. 1 A diagrammatically shown apparatus for producing fabricated parts, particularly inlays, onlays and crowns in dentistry, in a three-dimensional view.

FIGS. 2a and 2b A diagrammatically shown vertical section of a pattern and fabricated part holder.

FIGS. 3a and 3b A diagrammatically represented view of another embodiment of a pattern and fabricated part holder, FIGS. 2a and 3a showing the pattern holder.

FIG. 4 A diagrammatically shown vertical section through another embodiment of a holder for a pattern and fabricated part.

Figure 5B:

FIGS. 5a and 5b A diagrammatic view, partly in section, of a further embodiment of an apparatus for producing fabricated parts, in which the fabricated parts station with the machining tool is covered with respect to the remaining apparatus.

The apparatus for producing fabricated parts shown in FIG. 1 is designed for producing inlays, onlays and crowns in dentistry. The apparatus essentially comprises a copying mechanism 1, which is mounted in a support fork 2 and also a rocker 3, which carries a pattern station 4 and a fabricated part station 5. A foundation body 7 only diagrammatically indicated in FIG. 1 carries the support fork 2 and the rocker 3, which are both supported in a movable manner. The support fork 2 has two fork arms 8 between which is located the copying mechanism 1. The support fork 2 is pivotably mounted by means of two articulations 9 on a guide body 10, which is displaceably guided on a guide rod 12, whose ends are supported by means of uprights 13 on the foundation body 7.

In another embodiment in FIG. 1a the support fork 2 is connected in articulated manner to a pivoted lever 14, which is in turn pivotably mounted in a base 15 of the foundation body 7.

The copying mechanism 1 comprises a copying spindle 16, a feeler 17 with an e.g. pin or disk-like feeler body 18 and a toolholder 20 with a machining tool 22. The feeler 17 and the toolholder 20 are firmly interconnected, as is indicated in FIG. 1 by a connecting tube 21. The feeler body 18 and the machining tool 20 are pivotable together, e.g. by a rack and pinion drive about axes 19, 29 at right angles to the copying axis. The toolholder 20 carries a rotary, e.g. pin or disk-like machining tool 22, e.g. a diamond tool, which is driven by a not shown drive. The latter can e.g. be a driving head used in dentistry and having a turbine driving the machining tool 22. The driving head can be directly placed on the toolholder 20 and can also serve as a guide for the copying mechanism, or it can be positioned at a random point of the connecting tube 21 or on the feeler 17.

The rocker 3 is swivellable about a swivel axis 23, which is parallel to the copying axis 16. The pattern station 4 located on the rocker 3 carries as the pattern 24 an impression of a plastic defect replacement, on the basis of which is to be produced an inlay, an onlay or a crown, e.g. of oxide ceramic material. The feeler pin 18 senses the impression 24 and due to the identical movement of the feeler 17 and the toolholder 20 the displacement or deflection of the feeler pin 18 produces the same displacement or deflection on the machining tool 22. Thus, in a copying process it is possible to rough work the fabricated part 25 from its blank 25'. Both the impression 24 and the fabricated part 25 are rotatably mounted and mechanically interconnected with respect to the rocker 3, so that they can perform identical rotary movements. The rotation axes 26, 27 of the impression 24 and the fabricated part 25 are parallel to one another and therefore at right angles to the swivel axis 23, which intersects the two rotation axes 26, 27. The rocker 3 is mounted in support arms 28, which are in turn supported on the foundation body 7.

With the rotary movement of the machining tool 22, the apparatus according to FIG. 1 has eight movement axes, namely the three axes X, Y, Z by the copying mechanism 1, the swivelling movement about the copying axis 16, the swivelling movement of the feeler 18 and the machining tool 22 about axes 19, 29 at right angles to the copying axis 16, the movement about the swivel axis 23 of the rocker 3 and the rotary movements of the impression 24 and the fabricated part 25, i.e. seven movement axes inherent in the apparatus.

The feeler pin 18 is appropriately guided along the impression 24 manually through the guidance of the copying mechanism 1 with the aid of the driving head, whilst the other hand can bring the rocker 3 and the impression 24 into the desired copying positions. As a result of the manual operation of the feeler pin 18 and the manual adjustment of the impression 24 it is possible to copy without difficulty the most complicated three-dimensional shapes.

FIGS. 2a, b, 3a, b and 4 shows details of the rocker 3, FIGS. 2a and 3a showing the pattern station 4 and FIGS. 2b and 3b slowing the fabricated parts station 5. The two stations 4, 5 are rotatable about their vertical axes 26, 27, said two stations 4, 5 being interconnected by two not shown bevel gears in the rocker 3 and perform synchronous movements. The pattern station 4 has a base 30 onto which is screwed in vertically adjustable manner an adjusting sleeve 31. On the upper end of the adjusting sleeve 31 is located an impression holder 32, which can be secured by a screw cap 33. This makes it possible to centre the impression holder 32 even in the case of an impression 24 projecting to one side.

On the impression holder 32 the impression 24 is supported by means of a post 35, whose lower end 36 forms a frictional engagement with the holder 32 and is secured by a driver 37. The associated fabricated part station 4 carries a fabricated part blank 25', which is fixed to a holder 38, whose lower end 39 is held by frictional engagement in a base 40 and is provided with a driver 41. The base 40 need not be vertically adjustable. It is sufficient to be able to adjust the height of the impression 24 by the adjusting sleeve 31. The fabricated part 25 is rough worked by means of the impression 24 with the copying mechanism 1 from the fabricated part blank 25', where it is indicated in broken line form.

FIGS. 3a and 3b shows the production of a crown and the impression 24 is fixed by means of a ring carrier 43 to two supports 44 located on the base 30 of the pattern station 4. The ring carrier 43 has for this purpose two arms 45 with a bore 46, which is mounted on a pin at the upper end of the column 44, so that the impression 24 is positioned.

The crown is rough worked from the crown blank 25' with the aid of the impression 24 and the copying mechanism 1. To the crown blank 25' are fixed, e.g. bonded two arms 48, which are provided with bores 46 for mounting on the pin 47 of columns 44. The columns 44 are supported on the base 40 of the fabricated parts station 5. Into the crown blank 25' is worked a cavity 50, which facilitates the copying of the depression 51 for receiving the tooth stump. The impression 24 and the crown blank 25' are removed from the pins 47 and after rotating by 180° are mounted again and then the depression 51 for the tooth stump is copied in the crown blank 25'.

FIG. 4 shows a pattern station 4, which can optionally be used as a fabricated part station 5. A guide sleeve 52 is inserted in base 50 and secured by a resilient locking means 53. Driving slots 55 are formed in the bore 54 of the guide sleeve 52 and into them project driving pins 56 of a tubular driver 57. With the aid of a wire 59 passed through the driver 57 it is possible to press the post 35 and therefore the impression 24 out of the impression holder 67.

Onto the guide sleeve 52 is screwed a vertically adjustable adjusting sleeve 58, on whose upper face 66 is placed an impression holder 67 and is secured with a screw cap 33. The impression 24 is placed on a post 35, whose lower end 36 is inserted with frictional engagement in the impression holder 67 and is secured with a driver 37.

For the centring of the impression 24 a straightening member 69 i mounted on the base 30 and has in its apex a passage 70, with the aid of which the impression can be centred as a function of the dimensions of the blank 25' and then the screw cap 33 can be tightened. As a function of the size of the impression 24 a number of different straightening members 69 are available enabling the size of the blank 25' to be chosen just large enough to permit the rough working of the inlay, onlay or crown with minimum machining expenditure.

The apparatus variant shown in FIGS. 5a and 5b differs from that of FIG. 1 in that the fabricated part station 5 is located on a projecting end 72 of the rocker 3. The projecting end 72 of the rocker 3 projects into a cover casing 73, whose one wall 74 has a circular ring disk 75 and within this a circular disk 76. A passage 77 is arranged eccentrically in the circular disk 76 and through it projects the projecting end 72 of the rocker 3, whilst the pattern station 4 is positioned outside the cover casing 73. The rocker 3 can also be mounted on a single bearing means 71.

The circular ring disk 75 and the circular disk 76 are rotatable with respect to one another and are sealed by elastic sealing rings, cf. also the larger-scale FIG. 5b. The sealing ring 78 has prongs 79 between which grease is inserted. As a result the mobility of the two disks 75, 76 is ensured. A bellows 80 is fixed to a bore 81 in the circular ring disk 75 and through it projects the connecting tube 21 of the copying mechanism 1 connecting the feeler 17 and the toolholder 20.

It is necessary to use a cooling fluid 83 for machining the blank 25' and this collects on the bottom of the cover casing 73 and is drained off from there in not shown manner. As a result of the use of a cover casing 73 the remainder of the apparatus, i.e. the mounting means for the copying mechanism 1 which must be very precise in order to achieve an accurate shape of the fabricated part 25, and the rocker 3 is not dirtied by the cooling fluid. If the outer face of the impression 24 is also covered with a touching paint, which is removed when the feeler pin 18 passes over the pattern and therefore indicates whether said pin 18 has already passed over a point, this check is not impaired by splashing with the cooling fluid. The check to establish whether the entire impression surface has been covered can also be carried out in another way, e.g. by producing an electrostatic colour track, by discoloration as a result of a temperature difference, a chemical combination of two components or an electrochemical process.

As a result of the use of the two concentric disks 75, 76 there is no deterioration in the mobility of the toolholder 20 and the rocker 3. The separation of the machining side from the sensing side has the advantage that it is possible to isolate the machining tool drive noise and the fluid produced.

The described apparatus makes it possible to produce with great accuracy and in a short time inlays, onlays and crowns made from very hard materials, e.g. oxide ceramic materials and the patient only has to attend once for the complete treatment. The described apparatus is also suitable for producing complicated three-dimensional shapes.

We claim:

1. Apparatus for producing a fabricated part (25) worked by copying technology and in particular for producing inlays, onlays and crowns in dentistry, comprising
    a copying mechanism (1) having a feeler body (18) and a machining tool (22) and which is supported on a foundation body (7), having a rocker (3) with a pattern (24) adapted to be sensed by the feeler body (18) and a fabricated part (25, 25') adapted to be machined by the machining tool (22), the pattern and the fabricated part (25, 25') being rotatably mounted and mechanically and synchronously movably interconnected, the rocker being supported on the foundation body (7) and being swivelable about a swivel axis (23), which is at right angles to the rotation axes (26, 27) of the pattern (24) and the fabricated part (25, 25') and intersects the same.

2. Apparatus according to claim 1, characterized in that a support fork has a copying spindle (16) parallel to the swivel axis (23) of the rocker (3) and on which are axially displaceable and swivelable in a coupled together arrangement a feeler (17) with the feeler body (18) and a toolholder (20) with the machining tool (22).

3. Apparatus according to claim 2, characterized in that the machining tool (22) is driven by means of a toothed gear by a drive arranged on the toolholder (20).

4. Apparatus according to claim 3, characterized in that the feeler body (18) and the machining tool (20) can be swivelled about in each case one axis (19, 21) at right angles to the copying spindle (16).

5. Apparatus according to claim 2, characterized in that the copying spindle (16) is mounted in a support fork (2), which is supported with an articulation arrangement (9, 10; 14) for the vertical (Y) and horizontal (Z) adjustment of the copying spindle (16) on the foundation body (7), by a guide rod (12) carrying a guide body (10) with an articulation (9) or by a pivoted lever (14) mounted on a base (15).

6. Apparatus according to claim 1, characterized in that for fixing the pattern (24) and the fabricated part (25) to the rocker a pattern station (4) and a fabricated part station (5) are provided.

7. Apparatus according to claim 6, characterized in that the pattern station (4) has a rotary base (30) on which is supported in vertically adjustable manner an adjusting sleeve (31), to which is fixed the pattern (24) mounted on a post (35) by means of a horizontally displaceable holder (32, 67).

8. Apparatus according to claim 7, characterized in that the base (30, 40) has two columns (44) on which the pattern (24) or fabricated part blank (25') is supported by means of arms (45, 48).

9. Apparatus according to claim 8, characterized in that the arms (45) are fixed to a ring carrier (43) on which is anchored the fabricated part (24).

10. Apparatus according to claim 8, characterized in that the pattern (24) and fabricated part blank (25') are rotatable by 180° and can be supported with the aid of arms (45, 48) on said two columns (44), for copying a depression (51) on the back of the blank (25').

11. Apparatus according to claim 7, characterized in that the base (30) has a central bore (54), which is accessible from the underside of the rocker (3) and is used for ejecting the pattern (24) or fabricated part (25), by means of a wire (59).

12. Apparatus according to claim 1, characterized in that a fabricated part station (5) is located on a projecting end (72) of the rocker (3) and which is shielded with respect to a pattern station (4) by a cover wall (74) having a rotary circular ring disk (75) and a rotary circular disk (76), the end (72) of the circular disk and a toolholder (20) passing through the circular ring disk in a bellows (80).

13. Apparatus for producing a fabricated part (25) worked by copying technology and in particular for producing inlays, onlays and crowns in dentistry, comprising
    a copying mechanism (1) having a feeler body (18) and a machining tool (22) and which is supported on a foundation body (7), having a rocker (3) with a pattern (24) adapted to be sensed by the feeler body (18) and a fabricated part (25, 25') adapted to be machined by the machining tool (22), the pattern and the fabricated part (25, 25') being rotatably mounted and mechanically and synchronously movably interconnected, the pattern (24) and the fabricated part (25) being moved manually about the axes (26, 27) and about a swivel axis (23), the rocker being supported on the foundation body (7) and being swivelable about the swivel axis (23), which is at right angles to the rotation axes (26, 27) of the pattern (24) and the fabricated part (25, 25') and intersects the same.

14. Apparatus for producing inlays, onlays and crowns in dentistry, comprising:
  a support fork (2) being rotatably journaled on a guide body (12) that also moves slidably and pivotally on a guide rod (12) supported on a foundation body (7), the support folk (2) having a copying spindle (16) for mounting a feeler body (18) and a motor driven machining tool (22) that are firmly connected by a connecting tube (21) to move together; and
  a rocker (3) also being rotatably journaled about a swivel axis (23) extending substantially parallel to a copying spindle (16) and supported on the foundation body (7), the rocker (3) having a pattern (24) with an impression of a plastic defect replacement of the inlay, onlay or crown to be produced, and having a fabricated part (25) from which the inlay, onlay or crown is machined, the pattern (24) and the fabricated part (25) rotatably mounted respectively about rotation axes (26, 27) and mechanically and synchronously movably interconnected to perform identical rotary movements so that the entire outer surfaces of the pattern (24) and the fabricated part (25) revolve respectively about 360 degrees, the swivel axis (23) being at a right angle to the rotation axes (26, 27) of the pattern (24) and the fabricated part (25) and intersecting the same;
  whereby during copying of pattern (24) the feeler (18) senses the impression of the pattern (24) of the plastic defect replacement and due to the identical movement of the feeler (17) and a toolholder (20), displacement or deflection of a feeler pin (18) produces the same displacement or deflection of the machining tool (22).

15. Apparatus for producing inlays, onlays and crowns in dentistry, comprising:
  an outer circular ring disk (75) being mounted in a casing (73) and slidably rotatable therein, and having a connecting tube (21) projecting through it for mounting a feeler (17) with a feeler body (18) and a toolholder (20) that are firmly connected to move together; and
  a rocker (3) being mounted in a center circular disk (76) which is concentrically arranged within the outer circular ring disk (75) for moving slidably rotatable with respect to one another, and having a pattern (24) with an impression of a plastic defect replacement of the inlay, onlay or crown to be produced, and having a fabricated part (25) from which the inlay, onlay or crown is machined, the pattern (24) and the fabricated part (25) rotatably mounted respectively about rotation axes (26, 27) and mechanically and synchronously movable interconnected to perform identical rotary movements so that the entire outer surfaces of the pattern (24) and the fabricated part (25) revolve respectively about 360 degrees, around a swivel axis (23) being at a right angle to the rotation axes (26, 27) of the pattern (24) and the fabricated part (25) and intersecting the same;
  whereby during copying of pattern (24) the feeler (18) senses the impression of the pattern (24) of the plastic defect replacement and due to the identical movement of the feeler (17) and the toolholder (20), displacement or deflection of the feeler pin (18) produces the same displacement or deflection of the machining tool (22).

16. Apparatus as claimed in claim 15, wherein the outer circular ring disk (75) and center circular disk (76) are sealed by plastic sealing rings (78) having prongs (79) between which grease can be inserted.

* * * * *